(12) United States Patent
Плаβу et al.

(10) Patent No.: US 8,945,132 B2
(45) Date of Patent: Feb. 3, 2015

(54) DEVICE, SYSTEM AND METHOD FOR POSITIONING OR PREPARING THE POSITIONING OF A MEDICAL OPERATING INSTRUMENT

(75) Inventors: Norman Plaβy, Erfurt (DE); Timo Neubauer, Poing (DE); Manuel Millahn, München (DE); Blaine Warkentine, Long Beach, CA (US)

(73) Assignee: Brainlab AG, Feldkirchen (DE)

( * ) Notice: Subject to any disclaimer, the term of this patent is extended or adjusted under 35 U.S.C. 154(b) by 1713 days.

(21) Appl. No.: 12/030,302

(22) Filed: Feb. 13, 2008

(65) Prior Publication Data

US 2008/0195110 A1    Aug. 14, 2008

Related U.S. Application Data

(60) Provisional application No. 60/908,525, filed on Mar. 28, 2007.

(30) Foreign Application Priority Data

Feb. 13, 2007   (EP) .................................... 07102301

(51) Int. Cl.
| A61B 17/58 | (2006.01) |
| A61B 17/60 | (2006.01) |
| A61F 2/00  | (2006.01) |
| A61B 17/15 | (2006.01) |
| A61B 17/17 | (2006.01) |
| A61B 17/02 | (2006.01) |
| A61B 19/00 | (2006.01) |

(52) U.S. Cl.
CPC ............. *A61B 17/154* (2013.01); *A61B 17/155* (2013.01); *A61B 17/157* (2013.01); *A61B 17/1764* (2013.01); *A61B 2017/0268* (2013.01); *A61B 2019/5255* (2013.01); *A61B 2019/5268* (2013.01)
USPC .............................................. 606/88; 606/90

(58) Field of Classification Search
CPC ........................ A61B 17/1764; A61B 17/154
USPC .............................................. 606/87, 88, 90
See application file for complete search history.

(56) References Cited

U.S. PATENT DOCUMENTS

| 4,566,448 | A |   | 1/1986 | Rohr, Jr. |        |
|-----------|---|---|--------|----------|--------|
| 4,567,886 | A | * | 2/1986 | Petersen | 606/88 |
| 5,116,338 | A |   | 5/1992 | Poggie et al. |    |
| 5,540,696 | A |   | 7/1996 | Booth, Jr. et al. |    |
| 5,649,928 | A | * | 7/1997 | Grundei  | 606/88 |
| 5,662,656 | A | * | 9/1997 | White    | 606/88 |
| 5,669,914 | A |   | 9/1997 | Eckhoff  |        |

(Continued)

FOREIGN PATENT DOCUMENTS

| DE | 100 31 887 | 1/2002 |
| DE | 103 35 388 | 2/2005 |

(Continued)

*Primary Examiner* — David Bates
(74) *Attorney, Agent, or Firm* — Tucker Ellis LLP

(57) ABSTRACT

A positioning device for aligning at least one support on at least one structure includes a positioning tool configured to interface with a part of the structure, and a positioning element coupled to said positioning tool. The positioning element includes at least one holding part, wherein the at least one support is releasably coupled to said at least one holding part.

15 Claims, 21 Drawing Sheets

(56) References Cited

U.S. PATENT DOCUMENTS

| | | | |
|---|---|---|---|
| 5,911,723 A | 6/1999 | Ashby et al. | |
| 6,106,529 A * | 8/2000 | Techiera | 606/88 |
| 6,296,646 B1 | 10/2001 | Williamson | |
| 6,468,280 B1 * | 10/2002 | Saenger et al. | 606/88 |
| 6,478,799 B1 * | 11/2002 | Williamson | 606/90 |
| 6,551,325 B2 | 4/2003 | Neubauer et al. | |
| 7,029,477 B2 * | 4/2006 | Grimm | 606/88 |
| 7,727,238 B2 * | 6/2010 | Seo et al. | 606/88 |
| 8,162,949 B2 * | 4/2012 | Duggineni et al. | 606/88 |
| 2002/0068942 A1 | 6/2002 | Neubauer et al. | |
| 2002/0133163 A1 | 9/2002 | Axelson, Jr. et al. | |
| 2002/0198531 A1 | 12/2002 | Millard et al. | |
| 2003/0018338 A1 | 1/2003 | Axelson, Jr. et al. | |
| 2003/0069585 A1 | 4/2003 | Axelson, Jr. et al. | |
| 2003/0171757 A1 | 9/2003 | Coon et al. | |
| 2004/0249387 A1 * | 12/2004 | Faoro | 606/88 |
| 2005/0049486 A1 * | 3/2005 | Urquhart et al. | 600/429 |
| 2005/0075632 A1 * | 4/2005 | Russell et al. | 606/53 |
| 2005/0096535 A1 | 5/2005 | de la Barrera | |
| 2005/0149037 A1 | 7/2005 | Steffensmeier et al. | |
| 2005/0149041 A1 | 7/2005 | McGinley et al. | |
| 2005/0154394 A1 | 7/2005 | Michalowicz | |
| 2005/0203531 A1 | 9/2005 | Lakin et al. | |
| 2005/0261696 A1 | 11/2005 | Overes et al. | |
| 2005/0267482 A1 | 12/2005 | Hyde, Jr. | |
| 2005/0273115 A1 | 12/2005 | Coon et al. | |
| 2006/0036257 A1 | 2/2006 | Steffensmeier | |
| 2006/0064105 A1 | 3/2006 | Raistrick et al. | |
| 2006/0069389 A1 | 3/2006 | Knopfle | |
| 2006/0155294 A1 | 7/2006 | Steffensmeier et al. | |
| 2006/0235290 A1 | 10/2006 | Gabriel et al. | |
| 2006/0241639 A1 * | 10/2006 | Kuczynski et al. | 606/88 |

FOREIGN PATENT DOCUMENTS

| | | |
|---|---|---|
| DE | 10 2004 052228 | 6/2005 |
| DE | 10 2004 046 414 | 4/2006 |
| DE | 603 01 635 | 6/2006 |
| EP | 1 180 348 | 2/2002 |
| EP | 1 302 167 | 4/2003 |
| EP | 1 574 170 | 9/2005 |
| EP | 1 690 503 | 8/2006 |
| FR | 2 814 668 | 4/2002 |
| WO | 01/66021 | 9/2001 |
| WO | 03045256 | 6/2003 |
| WO | 2004/019792 | 3/2004 |

* cited by examiner

DEVICE, SYSTEM AND METHOD FOR POSITIONING OR PREPARING THE POSITIONING OF A MEDICAL OPERATING INSTRUMENT

RELATED APPLICATION DATA

This application claims priority of U.S. Provisional Application No. 60/908,525 filed on Mar. 28, 2007, which is incorporated herein by reference in its entirety.

FIELD OF THE INVENTION

The present invention relates to a apparatus, system and method for positioning a device or instrument, in particular for positioning the device or instrument relative to a system of coordinates or relative to a joint or a (bone) structure (e.g., a femur or tibia), or for positioning or preparing a position of a medical operating instrument (e.g., an incision block, a cutting block or a ligament balancing device).

BACKGROUND OF THE INVENTION

When attaching implants, such as artificial knee, elbow, finger or hip joints, it is required that the implant, such as a joint or part of a bone, is positioned as accurately as possible onto the adjacent bone. For this, the most accurate possible incisions must be made to the bone structures adjacent to the joint.

Referring to FIGS. 20A and 20B, U.S. Pat. No. 6,551,325 B2 discloses that a tibial incision block 100 is navigated onto a bone K using a positioning element inserted into a guide slit 100a. Then this incision block 100 can be fixed to the bone K with suitable fixing or holding elements 101. Using a cutting tool 102, a desired incision in the incision plane S0 can be made either by placing a blade on the upper side of the incision block 100, as shown in FIG. 20A or by guiding a blade in the guide slit 100a, as shown in FIG. 20B.

A drill template can be positioned by a reference star on the incision plane S0 shown in FIG. 20A in such a way that suitable tools for creating a connecting structure between the bone and the incision block, for example holding elements 103, are inserted through holes into the bone K, such that a second incision block 104, as shown in FIG. 21, can be correctly positioned by attaching it to the holding elements 103. In the same way, a holding element 103, for example, also can be firmly connected to the incision block 104 in such a way that the incision block 104 can be inserted into holes drilled into the bone K with the aid of the drill template, using the holding elements 103. Once the second incision block 104 has been placed in the desired position, the desired incisions in the planes S1 to S4 may be made through the various guide slits provided in the second incision block 104.

An artificial joint can be attached onto the bone, in which the desired incision planes S0 to S4 have been created with the help of the first incision block 100 and the second incision block 104, said joint being correctly positioned when the location of the incision planes S0 to S4 is correct.

US 2006/0036257 A1 discloses a tibial spacer block used during knee arthroplasty and configured to be temporarily positioned upon a resected proximal portion of a tibia for performing a range of motion analysis and for checking flexion and extension gaps prior to cutting the distal or posterior femur. The spacer block includes an attachment arrangement configured and arranged to mate with a complementary attachment arrangement of an alignment tower and/or a femoral cutting guide. The alignment tower, which is configured to be used with an alignment rod, can be used for verifying the alignment of the limb's mechanical axis when the spacer block is positioned between the tibia and the femur. The femoral cutting guide can be used for guiding a cutting member into proper orientation for resecting a distal or posterior portion of a femur.

DE 103 35 388 A1 discloses that an area in which a surgical procedure is to be performed is connected to a navigation system with several transmitting and receiving devices. A marker in the shape of a rigid body is joined to the femur with a unit assembled of a sleeve and a holding element. The sleeve is fitted with a cylindrical extension with a conical tip, engaging with a matching recess located at a bone plate attached to the femur in order to facilitate a safe connection.

DE 100 31 887 A1 discloses an optical system that detects anatomical parameters of a leg of a patient and detects leg movement data indicative of the original movement range of the leg. A computer system determines the original knee kinematics for the knee to be treated from the detected anatomical parameters and the movement data, and selects prostheses for the knee based on the original knee kinematics.

U.S. Pat. No. 4,566,448 discloses a ligament tensor and distal femoral resector guide which includes an adjustable support member for mounting on a tibial cutting guide including a guide slot in which is reciprocally mounted a slide member. The slide member has an arm extending outward therefrom for engaging the condylar notch between the femoral condyles and a screw member. The screw member threadably engages the slide member and can be used for adjusting the position of the slide member and arm relative to the tibia cutting guide head to establish tension in the ligaments of a knee structure. A flat pressure plate is removably mounted in the slots of the tibia cutting guide head for engaging the sectioned tibia plateau for applying pressure to the tibia for tensioning of the ligaments. A cutting guide head for guiding the resection of distal femoral condyles is mounted on the adjustable support member.

US 2005/0149037 A1 discloses a cut block for cutting the femur and tibia during knee replacement surgery.

U.S. Pat. No. 5,911,723 discloses a surgical tensioning apparatus that has a base, first and second bone tissue engaging elements mounted on the base and being displaceable toward and away from each other. One of the tissue engaging elements is adapted to be oriented by the tissue engaged thereby. A guide element is provided that is adjustable in relation to the base and one of the tissue engaging elements for positioning a first location element to locate a cutting guide provided with cooperating second location element onto the bone to be resectioned.

SUMMARY OF THE INVENTION

A positioning or aligning device for aligning or positioning at least one and preferably two or even more devices or bases at a bone, such as for example the femur or the tibia, comprises a positioning tool that can have a recessed portion (e.g., a spoon-like shape). This positioning tool is preferably an elongated element and, for example, can have a recessed portion. Preferably, the recessed portion has a generally concave shape (e.g., the elongated element can be curved in a lateral direction and can have a rod-like shape). A generally concave portion, as used herein, refers to a curved surface that is not necessarily symmetrical with respect to a central axis of the elongated element. For example, a first half of the elongated element can exhibit more or less curvature than a second half of the elongated member. Further, the curvature may only be present along a length or width of the elongated element.

Preferably a cross-section of the positioning tool has a U-shaped form. The positioning tool is preferably not curved in the longitudinal direction and is connected to a positioning element that can be slideable, movable or relocatable on the positioning tool, preferably in the longitudinal direction of the positing tool. In an embodiment the positioning element can have a hole or guiding recess corresponding to the shape of the positioning tool. This hole preferably has a shape corresponding to the cross section of the positing tool in the lateral direction, so that the positioning element is supported and axially or longitudinal shiftable on the positioning element.

The positioning tool having, for example, a recessed portion as mentioned above, can be inserted into the joint, e.g., a knee gap. The positioning tool is preferably inserted after removing cartilage from the joint, so that the positioning tool has a stable position in the joint or knee gap defined by the knee joint e.g., by the shape of the condyles of the femur which are then placed in the concave-shaped portion of the positioning tool. On the opposite surface the positioning tool abufts the tibia and thus, the recessed positioning tool can be stablely held between the femur and the tibia when the leg is in a stretched or fully extended state.

Having the positioning tool inserted into the joint, the positioning tool can be exactly or approximately in a plane that is orthogonal to the longitudinal direction of the femur and/or the tibia when the leg is in a fully extended or stretched state. After positioning the positioning tool, the positioning element can be shifted on the positioning tool until one or two bases being releasably coupled to the positioning element are placed at or on a respective part of a bone, e.g., the femur and the tibia. The positioning tool also can be connected to the positioning element, which, for example, can hold two bases, and the positioning tool can be inserted into the joint or knee gap until one or each base held by the positioning element is located on or at the bones defining or forming the joint.

The preferably recessed device thus can serve as an alignment instrument that is partly or fully pushed into the uncut knee joint gap. The device aligns to the femoral condyle, which defines the position of the tibial and the femoral array's base. This position should optimally be adjustable to different knee sizes.

The position of the array bases on the alignment instrument is chosen in a way that, after the instrument is aligned in the joint gap and the bases are fixed to the bone, they prealign the cutting block. The cutting block therefore only needs fine adjustment and thus the navigation of the rough position on the bone can be omitted.

In another version, the recessed portion can be extended by an interface to attach a cutting block mechanism directly to the recessed portion. After the adjustment, the cutting slot is fixated to the bone. The recessed portion with the attached mechanism is then removed from the bone or joint gap before performing the cut.

The at least one positioning element comprises at least one and preferably two base holding parts, which can be arms, a hole or pins at the positioning element. Preferably the base holding part is formed in a way to allows attachment or insertion of a base holding element, such as for example a base holding pin or hole, in only a single predefined orientation or direction. For example, the base holding part can be a hole having a trapezoid-shape corresponding to a pin also having a corresponding trapezoid-shape that allows insertion of the pin into the hole only in a single orientation.

The positioning device can be used for a surgical method such as for example preparing an initial set-up of cutting blocks for generating one or more incision surfaces for an artificial joint, such as surfaces S0 to S4 shown in FIGS. 20A, 20B and 21, for example. The bases can be used for determining an initial orientation for cutting blocks or cutting jigs, which can be attached to the bases and which thus can be positioned at a bone in a predefined area or location on or at the bone. This eliminates the need of providing a workflow for finding a good or suitable position to place these cutting blocks, for example, by adjusting the position of these cutting blocks with the aid of reference stars.

Thus, the inventive positioning device can be used to reduce the number of steps when positioning a base for a surgical tool or when positioning the surgical tool itself, such as a cutting block. Hence the time needed for positioning a surgical tool and the invasiveness associated with attaching surgical instruments to the bone can be reduced.

A positioning system in accordance with the invention comprises a positioning device having a positioning tool and a positioning element as set forth above, together with at least one and preferably two bases having holding elements, such as holes or pins, to be detachably connected to the positioning element. Via the positioning device, the base or bases can be positioned at a predefined location at a structure or bone with respect to the joint. The bases can be fixed or attached to the respective structure or bone using a fastener (e.g., a screw fastener or the like), preferably a uni-cortical screw, in a predefined orientation with respect to the bone and/or the joint. The positioning element can thereafter be removed together with the positioning tool, so that using the positioning device a predefined location for each base can be easily determined and found. The predefined location is preferably determined by the form of the positioning tool and the positioning element, and is preferably selected to ensure that if the bone or bones at or to which the bases are attached are in a predefined state (e.g., a stretched or fully extended leg). Then navigation instruments, such as a reference star, and/or surgical tools, such as a cutting block or cutting jig, can be attached to the respective base and thus to a bone so as to have a good or optimal position for later navigation or surgical steps.

Preferably reference elements or a reference star can be attached to each base being positioned using the positioning device. This can provide an orientation that enables a navigation system or camera to detect the reference elements in the predefined orientation determined by the position of the bases. If, for example, a patient and his leg have a known position and if there is a known position for an IR-camera, complicated and time consuming setup need not be performed when using the positioning system for positioning and adjusting the orientation of reference stars at the respective bones to ensure good visibility of the reference stars.

To fix the base(s) to the structure or bone, it is preferred to have an optimized screwdriver that allows for easy fixating of the screws for the bases of the reference arrays, preferably having a magazine for holding screws to avoid difficult reloading of the screws.

It is possible to provide a reference array base holder that enables simple attachment of the arrays if the use of the recessed tool is not possible. If the array base and cutting block mechanism have the same interface, the tool also can be used for easily holding the cutting block mechanism in place.

The array bases are preferably formed as bone plates that can be attached to the bone by screws, wherein the screws may be uni- or bicortical. The arrays can have spikes or protruding elements at a surface that contacts the bone or can have a toothed or serrated surface to secure the respective base against rotation (i.e., to avoid rotational movement on the bone when or after the arrays are attached).

The bases are preferably designed in a way that soft tissue may cover part of the base after it has been attached to the bone to thus be a subcutaneous bone plate. The bone plates can have two different interfaces. One can be used for attaching a reference geometry and the other can be used to attach a cutting block. Both interfaces preferably prohibit rotational movement and are designed as quick-release connections.

According to a further aspect of the invention, a ligament balancing device is provided that can guide a cutting device, such as a cutting block or a cutting jig. Alternatively, or in addition, the ligament balancing device also can be provided with or connected to a reference or tracking element, such as a tracking array, having for example three respective reference elements.

The ligament balancing device includes a spreader, which can be extended by a tracking array that is fixedly mounted on the spreader, preferably on the spreader's tibial plateau. Due to a known position of the array on the spreader, the lowest plane of the spreader-paddles having contact to the cut tibial plane can be calculated. The plane then matches with the cut tibia plateau. This makes the previously attached reference array on the tibia unnecessary, because the cut tibia plane has been verified and therefore can be used as a reference plane. Furthermore, the spreader can be provided with the same interface as the array bases, so that the cutting block with the corresponding interface can also be attached to the spreader.

Thus, the system, device and method in accordance with the invention can improve the use of instruments, such as instruments used for total knee arthroplasty, by optimizing a workflow that results in less duration and employs less complex instruments. Furthermore, the invasiveness typically associated with use of certain instruments can be decreased. This can reduce time expended in performing navigated surgeries by reducing the amount of navigational steps that have to be performed in a total knee arthroplasty.

The alignment of the bases via the recess is an easier way for setting the rough navigation of the cutting block and hence saves time. Furthermore, a location for the array bases is known. The arrays do not need joints that have to be adjusted, as the setup is predefined.

Due to the combined bases including interfaces for a reference array and for a cutting block, it is possible to reduce the amount of pins/screws/nails that are necessary, hence time is saved as well as the invasiveness is reduced. Regarding the invasiveness, the possibility of attaching the cutting block to the same fixation as the reference array not only saves additional drilling into the bone, but also eliminates the need for additional incisions. Furthermore, the length of the incision (s) might be reduced, as the area of contact between the bone and the baseplate is designed to lie subcutaneous.

BRIEF DESCRIPTION OF THE DRAWINGS

The forgoing and other features of the invention are hereinafter discussed with reference to the drawing.

FIG. 13 illustrates alignment of the rod to the mechanical axis of the leg; FIG. 14 illustrates fixation of the tibial base to the bone; FIG. 15 illustrates alignment of the rod to the mechanical axis of the leg (femur); FIG. 16 illustrates fixation of the femoral base to the bone (tibial base is already fixed); and FIG. 17 illustrates the tibial and femur bases fixated to the bones, wherein the tool has been removed.

DETAILED DESCRIPTION

Figure 1:
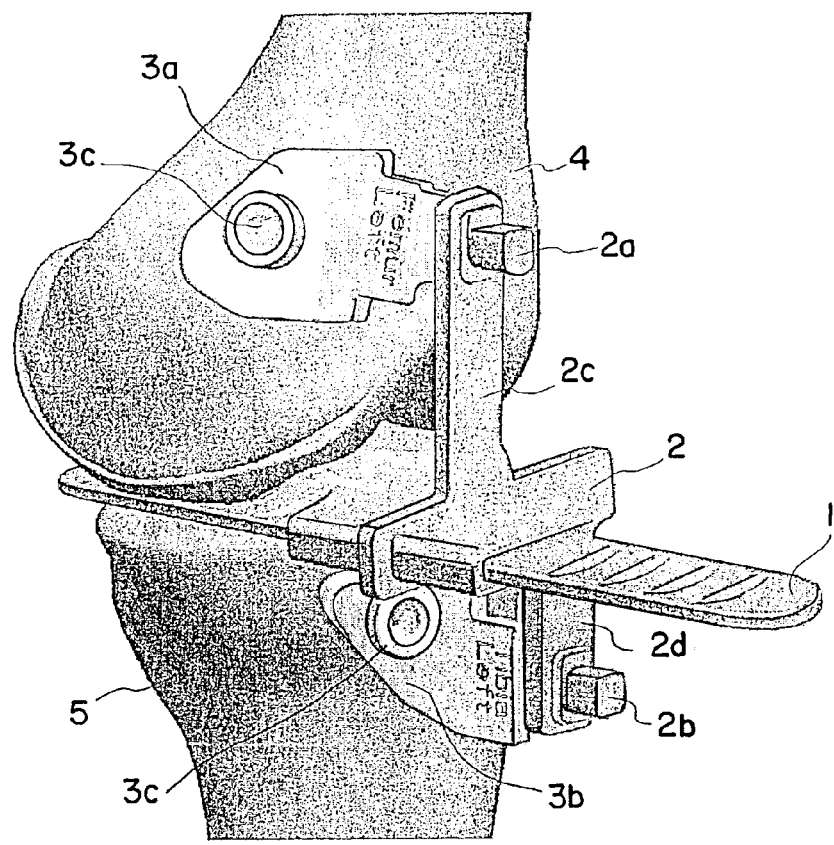
FIG. 1 shows the alignment of two bases using an exemplary positioning tool in accordance with the invention.

Referring to FIG. 1, alignment of the bone plates or bases 3a and 3b on the femur 4 and the tibia 5, respectively is shown. The bone plates or bases 3a and 3b (e.g., a support, mount, anchor or the like) are arranged on and connected to the positioning tool 1, which is a recessed instrument that aligns itself on the anatomical structures of the femoral condyles. The recessed tool 1 is pushed into the joint gap of the knee between the femur 4 and the tibia 5 in order to have a defined position and orientation with respect to the femur 4 and tibia 5 when the leg is fully extended. The slidable positioning element 2 is shiftable in a longitudinal direction on the recessed positioning tool 1. In an alternative embodiment, the slidable positioning element 2 can be fixed to the recessed positioning tool 1. The slidable positioning element can include two arms 2c and 2d extending away from the positioning tool 1, wherein the arms 2c and 2d includes pins 2a and 2b, respectively, wherein the pins are on one side of the arms 2c and 2d. Additional pins (not shown in FIG. 1) can be included that extend in the opposite direction with respect to the arms 2c and 2d. The bases 3a and 3b can be releasably coupled to these additional pins in a predefined orientation. This orientation can be determined or set by the shape of the pins and corresponding holes 3d (shown in FIG. 6) that are used to attach bases 3a and 3b. When the slidable positioning element 2 is shifted toward the bones 4 and 5, the bases 3a and 3b are brought with a predefined orientation, determined by the position of the positioning tool 1, into contact with the femur 4 and the tibia 5.

Figure 2:
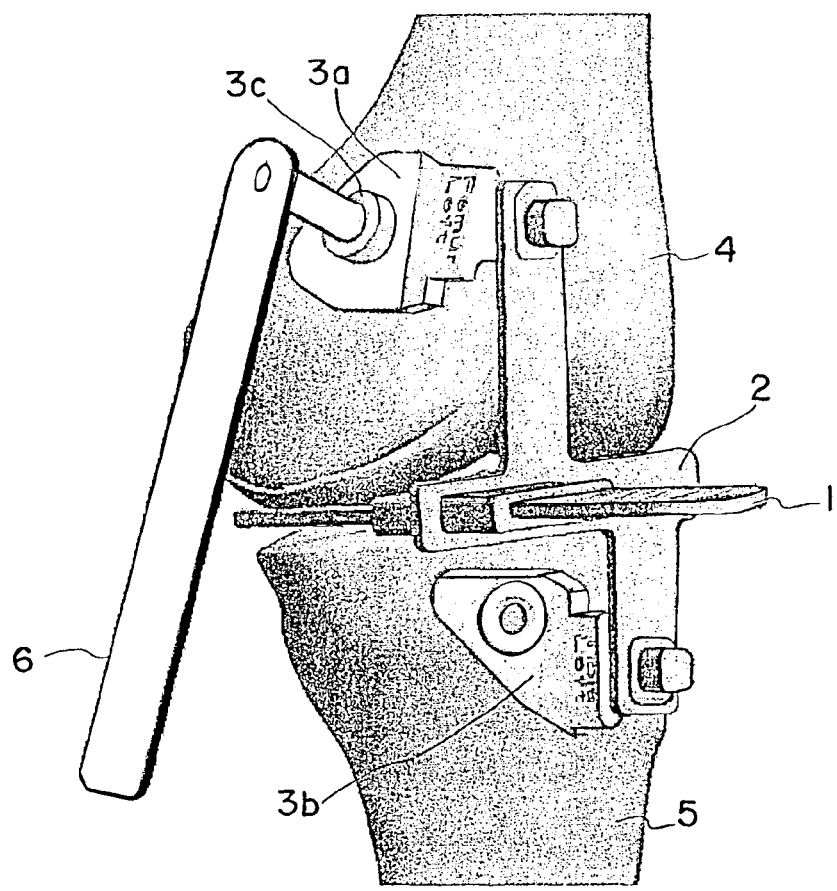
FIG. 2 shows a drill guide attached to an opening of the base for drilling a hole into the bone.
Figure 3:
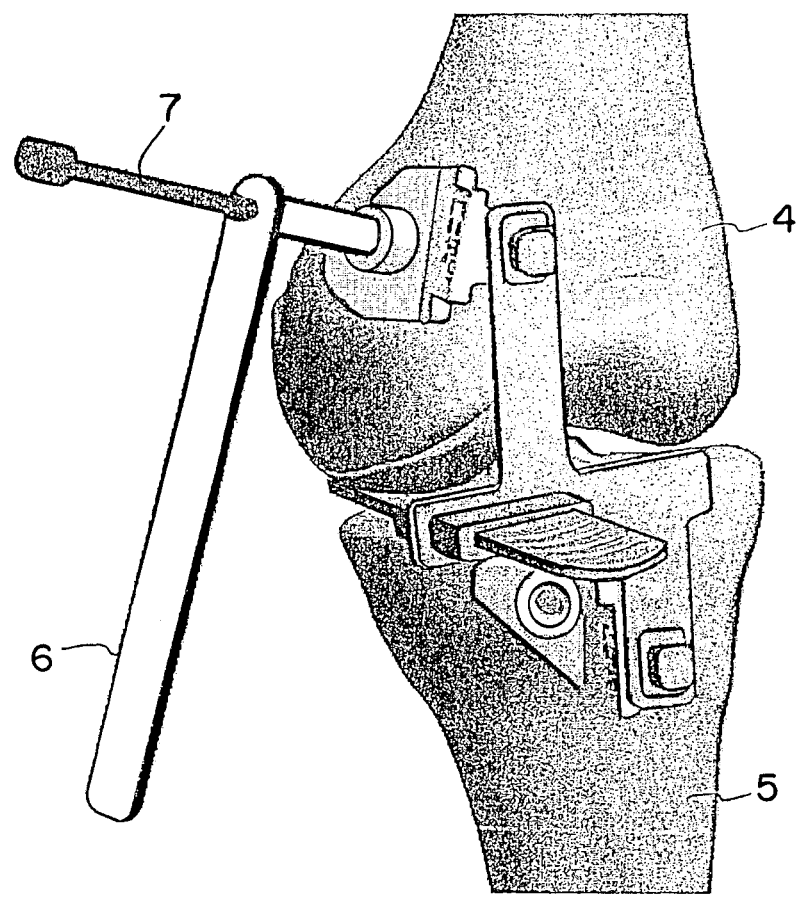
FIG. 3 shows drilling of the bone using the drill guide of FIG. 2.
Figure 4:
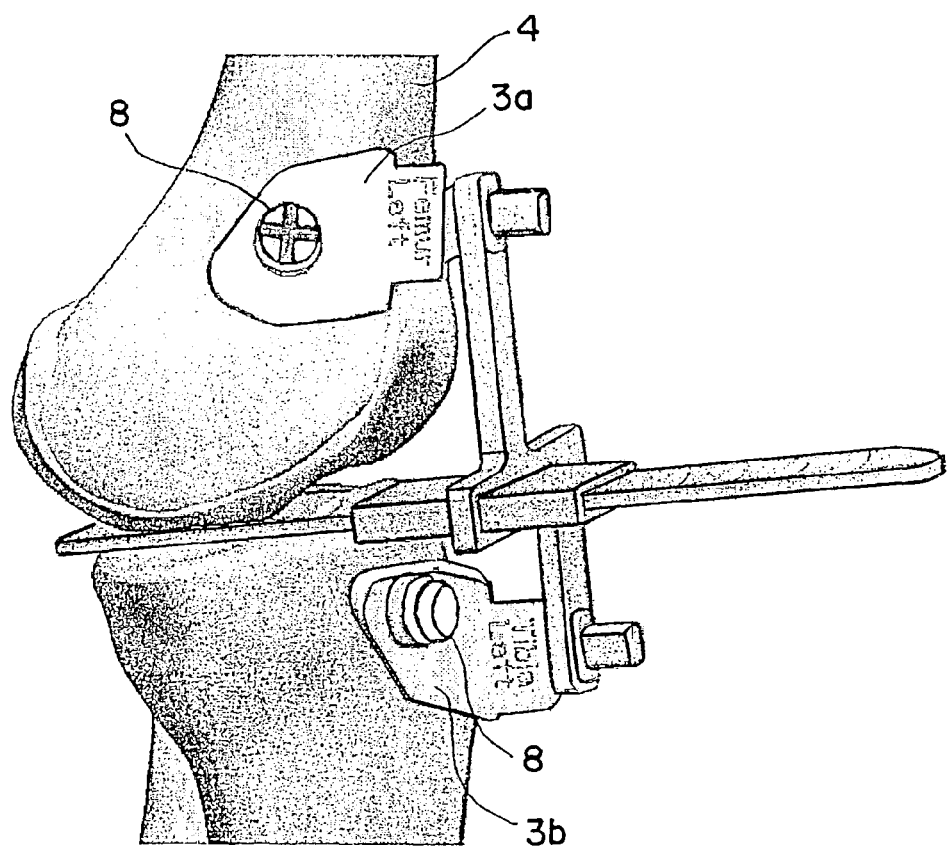
FIG. 4 shows the exemplary bases attached to the bone using one screw for each base.

Each base 3a and 3b is provided with an opening or a hole 3c, which can be used as guidance for a drill guide 6, as shown in FIG. 2, which can be used in the event that the guiding length of the holes 3c in the baseplate 3a and 3b is not long enough to properly guide drill 7. The drill guide 6 is inserted into each hole 3c of the bases 3a and 3b to provide a guide for a drill 7, as shown in FIG. 3. A hole is drilled into the femur 4 and the tibia 5 for fixing the bases 3a and 3b to the bone (after removing the drill guide 6 and the drill 7). The bases 3a and 3b can be held in place using a single screw 8, as shown in FIG. 4.

Figure 5:
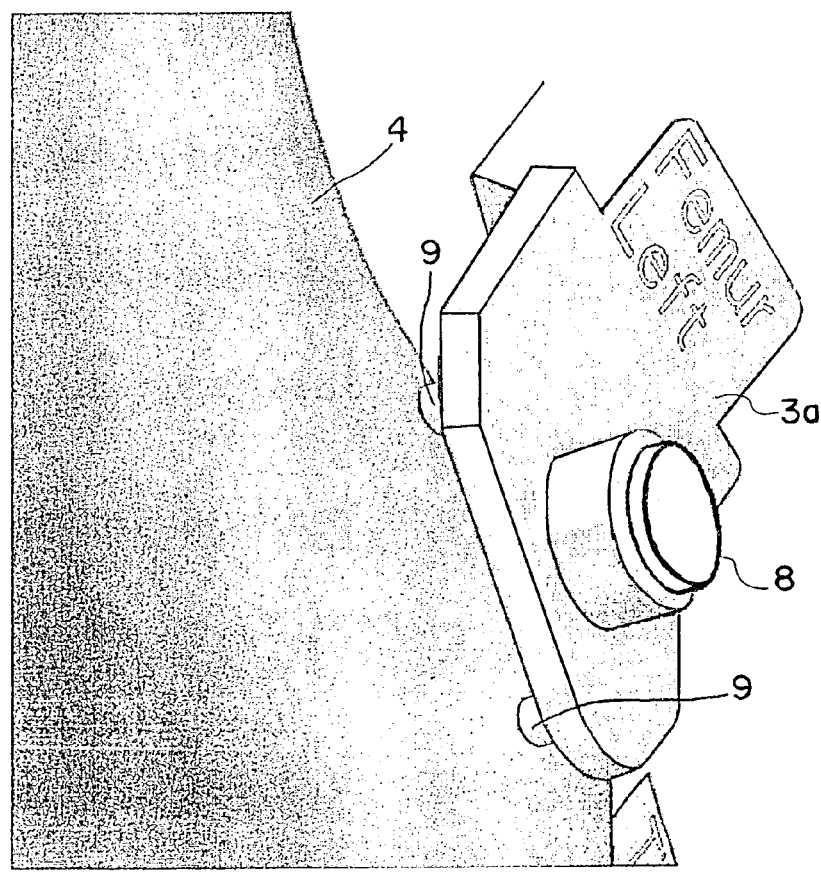
FIG. 5 shows exemplary spikes on the back of the base to inhibit rotational movement of the base.

As shown in FIG. 5, spikes or a toothed surface having toothed elements 9 can be provided at the surface of each base 3a and 3b to prevent rotational movement of the respective base after being attached to a respective bone 4 and 5 via screw 8. After the bases 3a and 3b have been fixed to the bones 4 and 5, the positioning tool 1 can be removed together with the positioning element 2, so that the bases 3a and 3b are only held at the bones 4 and 5 by means of the screws 8 and optionally using the spikes 9 or a toothed surface to prevent rotation of the bases.

Figure 6:
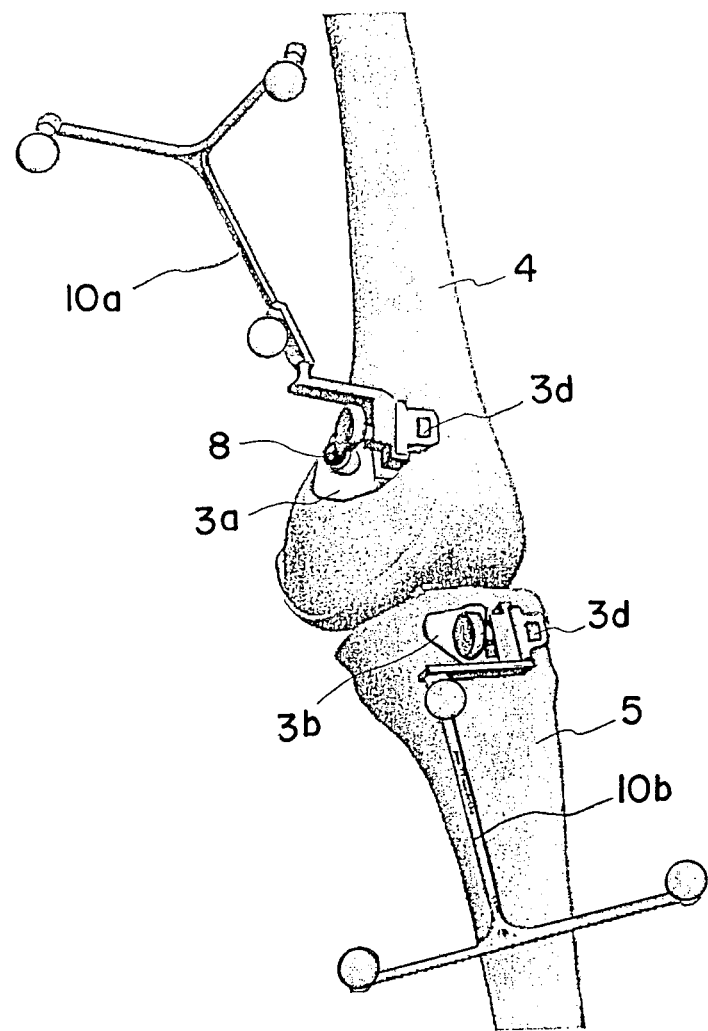
FIG. 6 shows the alignment of the bases together with attached reference arrays on the tibia and the femur.
Figure 7:
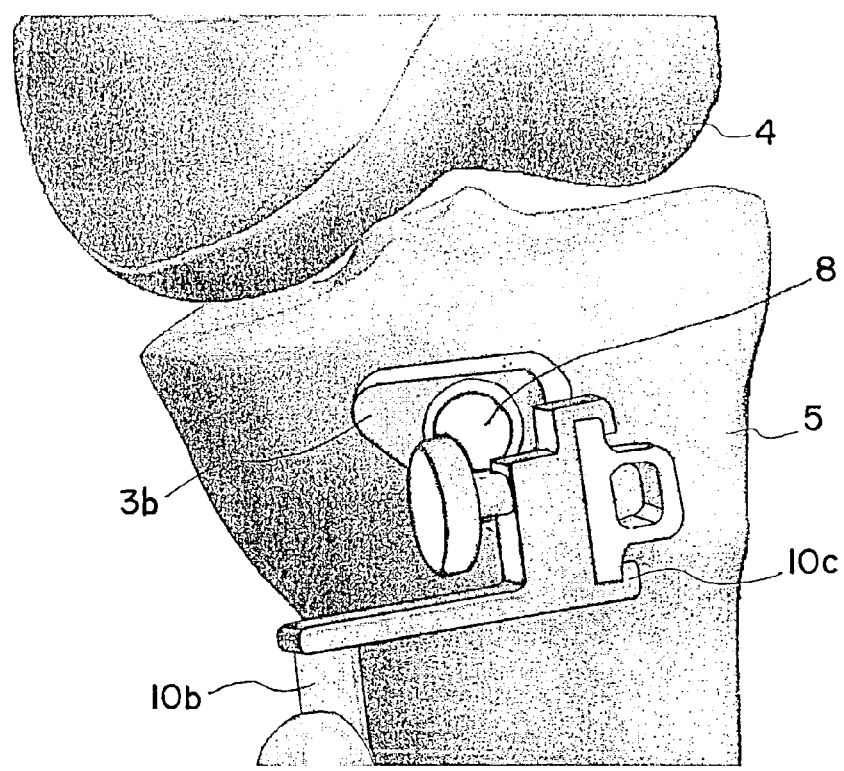
FIG. 7 shows an exemplary quick-release attachment of the reference arrays to the base.
Figure 8:
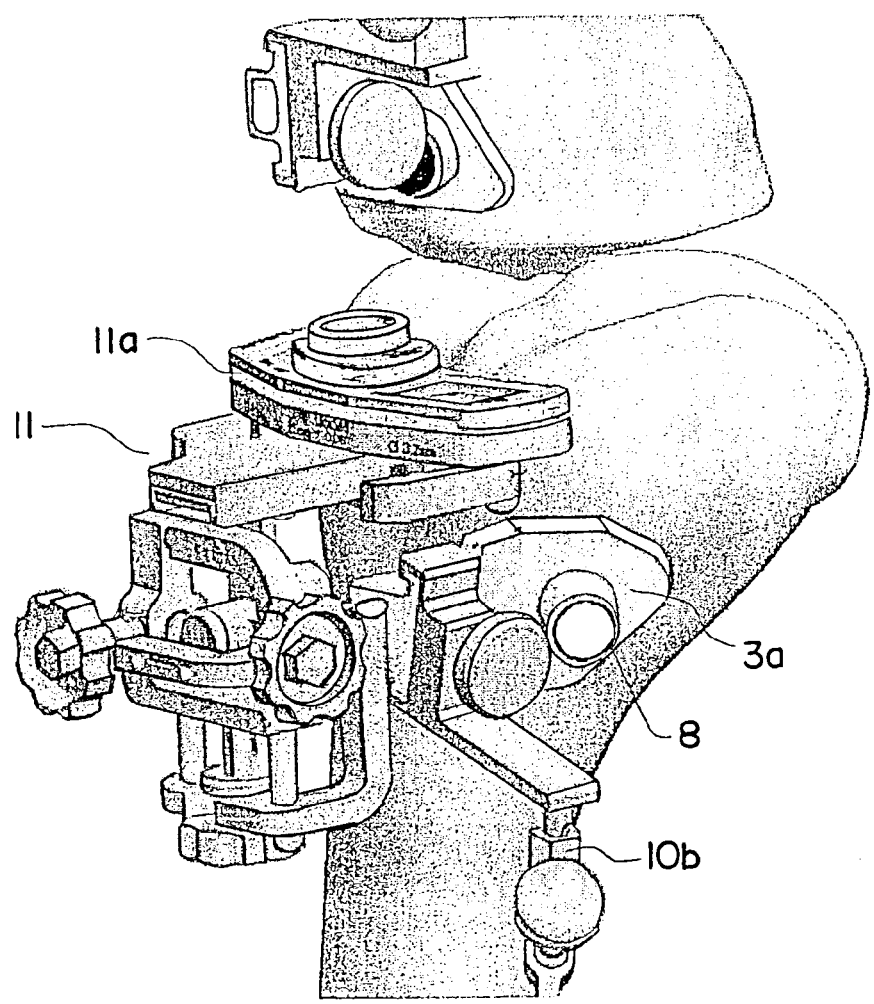
FIG. 8 shows the attachment of a cutting block to the femoral base.

As shown in FIG. 6, the bases 3a and 3b can be further aligned with reference arrays 10a and 10b, which can be attached to the bases 3a and 3b using a sliding and fixable connection 10c as shown in FIG. 7. It is possible to first loosely insert the screws 8 for rough alignment or attachment of the bases 3a and 3b. Once roughly aligned and/or attached, the bases 3a and 3b can be finely aligned via the reference arrays 10a and 10b, and the bases then can be fixed to the bone by fully tightening the screws 8.

Figure 11:
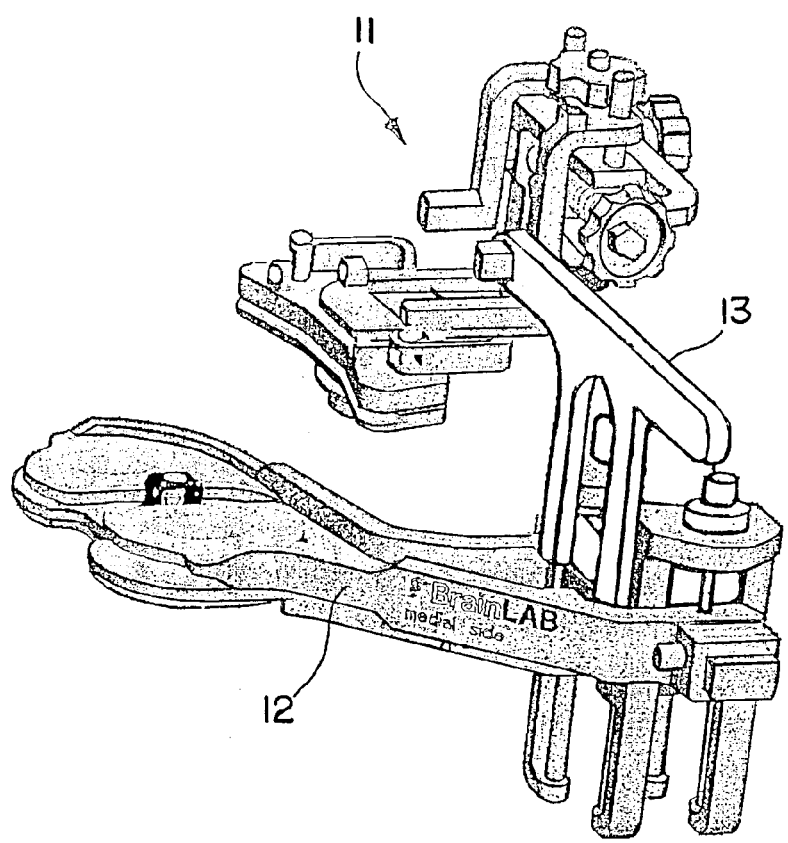
FIGS. 11 and 12 show an exemplary ligament-balancing device that has been provided with an interface in order to receive and align a cutting block.

After the bases 3a and 3b have been aligned, a cutting block 11 having a slot 11a for guiding a cutting blade can be attached to one baseplate, e.g., the femoral baseplate 3a, as shown in FIG. 11. To provide connectability to the cutting block 11, the base or bone plate 3a can be supported with an interface that fits to the interface of the cutting block 11 and that is locked against rotation.

The reference arrays 10a and 10b can have a fixable connection 10c formed as quick connect interface 10c. In order to attach the arrays 10a and 10b to a baseplate attached below the skin, the leg shall be moved to extension where the incision can be moved aside, so that the baseplate can be attached. After the bone plate has been fixated, the soft tissue lies over the baseplate. The higher parts of the baseplate also have a retracting function to the soft tissue.

Figure 9:
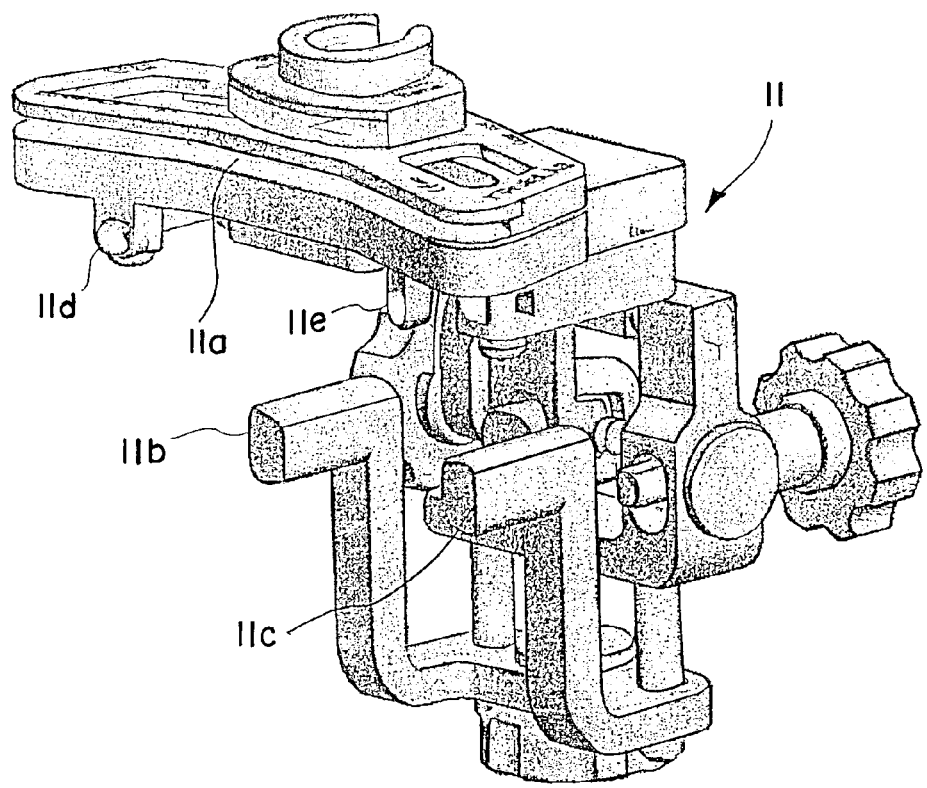
FIG. 9 shows a version of the fine-adjusting mechanism for the cutting block that is provided with interfaces.

FIG. 9 shows a version of a fine adjustable mechanism of the cutting block 11 that is provided with interfaces 11b and 11c. Depending on which knee joint, i.e., the left or the right knee joint, is to be replaced, the left or the right interface 11b or 11c can be used. The cutting block 11 can be attached for generating the tibial cut in one of the following ways.

The recessed positioning tool 1 can be inserted again with the leg being in extension. Preferably the positioning tool 1 is fixed with one additional screw, such as a uni-cortical screw. Then the cutting block is 11 is attached thereto.

Having the mechanism on the femoral side, the femoral array could be detached to provide space for the mechanism used in making the tibial cut, or the femoral array can be removed and the mechanism for the tibial cut can be attached to the base of the femoral array. Alternatively, the mechanism for the tibial cut can be attached to the tibial base, which contains an interface that couples with a corresponding interface at the mechanism. The tibial cutting block or cutting jig 11 then can be fixed with at least two pins, nails or screws, which can be inserted trough openings 11d and 11e to the tibia 5.

Figure 10:
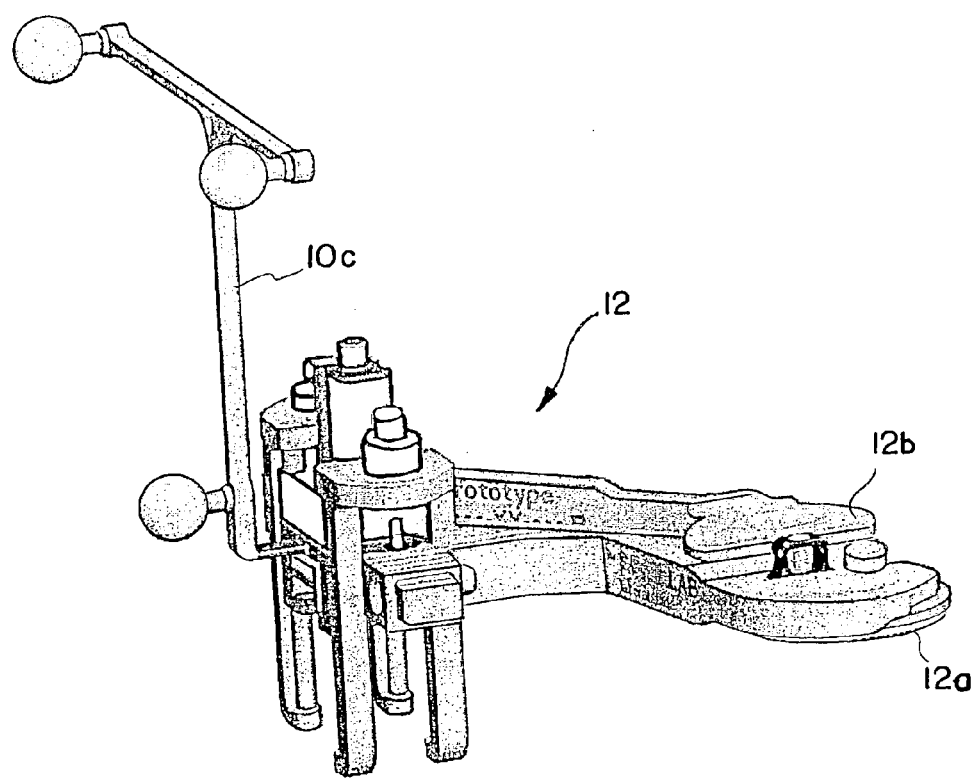
FIG. 10 shows an exemplary ligament-balancing device (spreader) onto which a tracking array has been fixedly attached.

Thereafter, the recessed positioning tool 1 can be removed from the base with or without the mechanism, if necessary, and the tibial cut can be performed. After performing the tibial cut, ligament balancing can be performed in flexion and extension using the ligament balancing device 12 as shown in FIG. 10 provided with a tracking array 10c. The ligament balancing device 12 is inserted into the joint gap and/or can be attached to the tibia component. The ligament balancing device 12 or spreader provided with the tracking array 10c provides the possibility to calculate the position of the underside of the spreading paddles 12a, 12b and thus the orientation of the cut-plateau 5a of the tibia 5 which has been previously verified.

Figure 12:
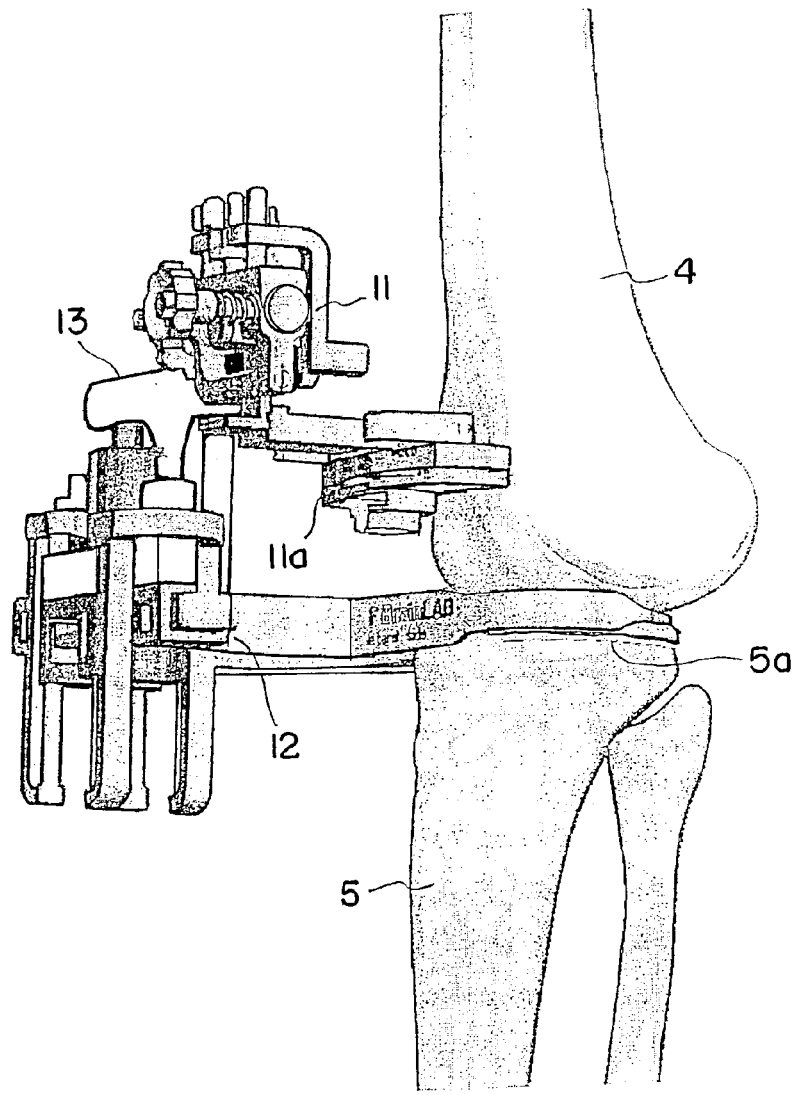
Figure 13:
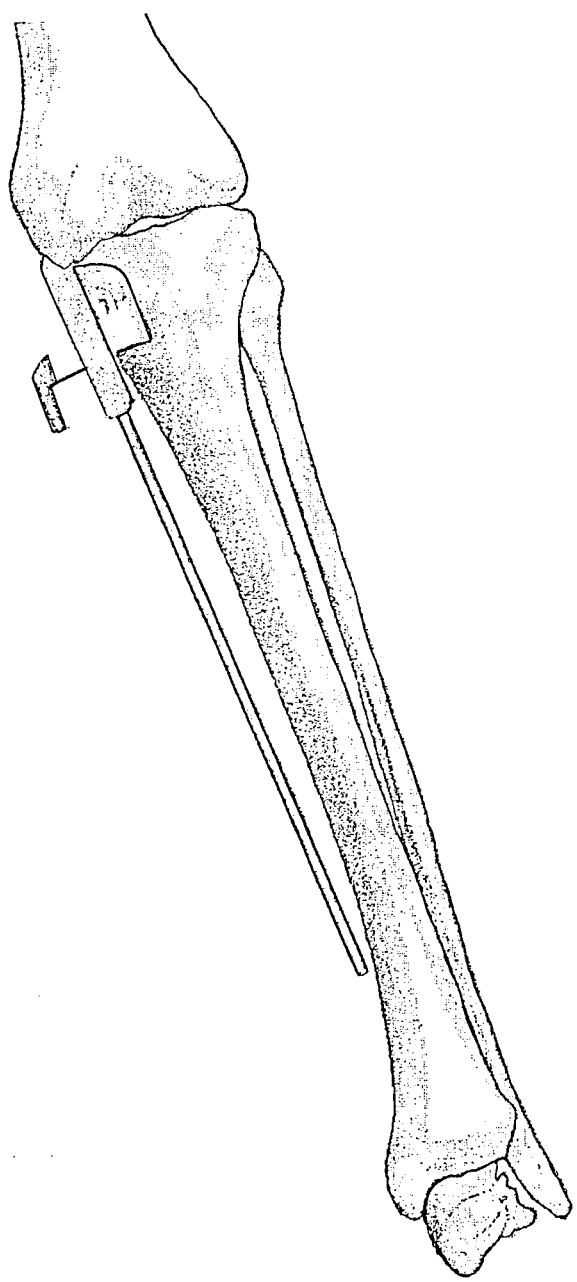
FIGS. 13 to 17 show en exemplary positioning tool that is used for a sequential attachment of the bases. The long rod is meant for an alignment on the mechanical axis of the leg. After one base is fixated to the bone, the second base is attached to the tool and the tool is rotated by 180 degrees and again aligned on the leg-axis.
Figure 14:
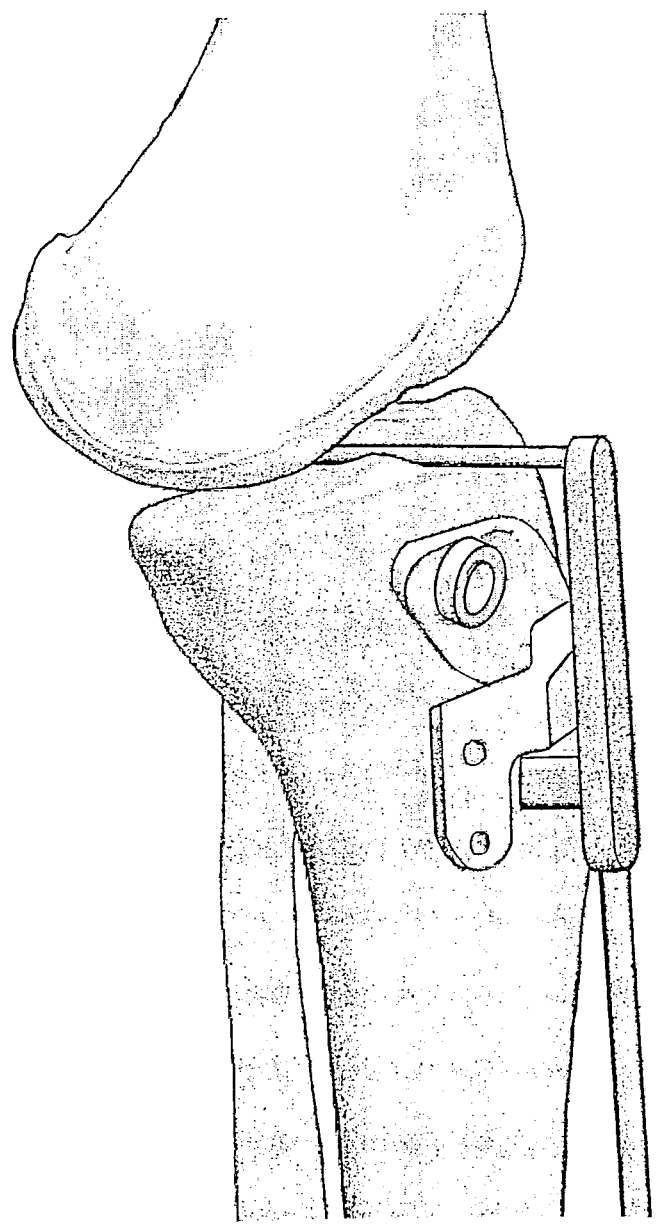
Figure 15:
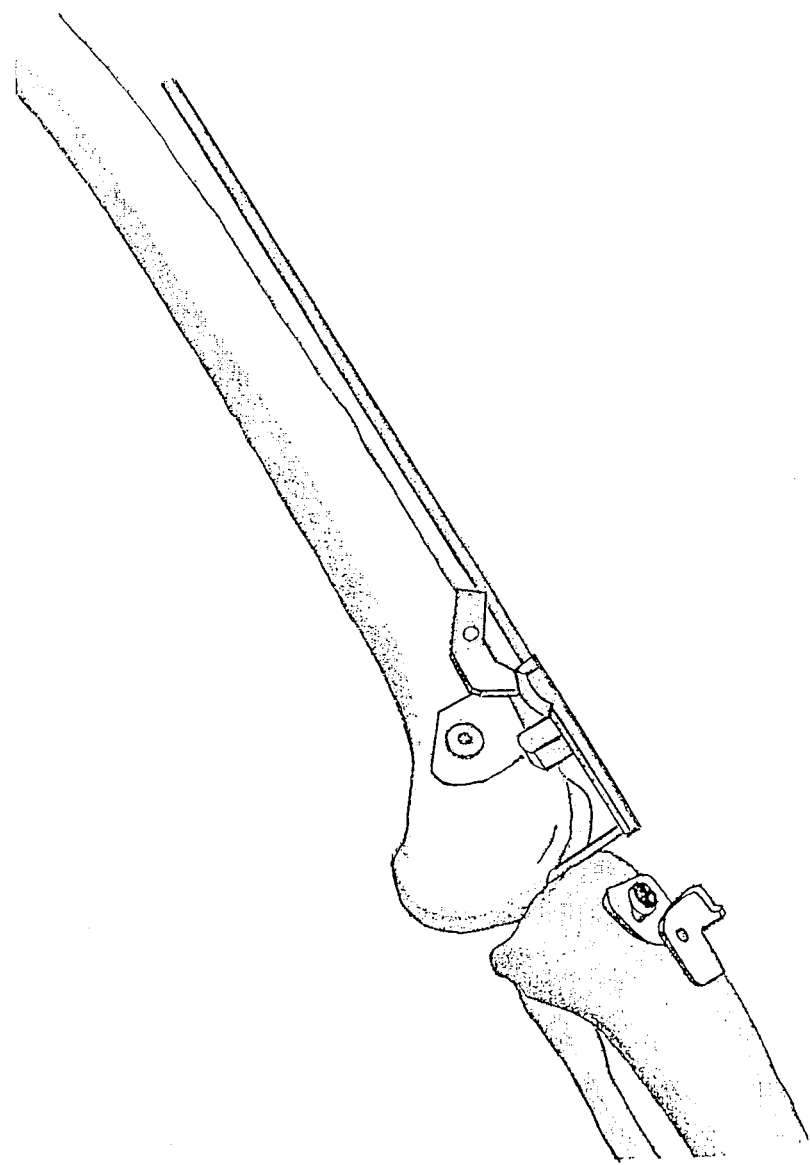
Figure 16:
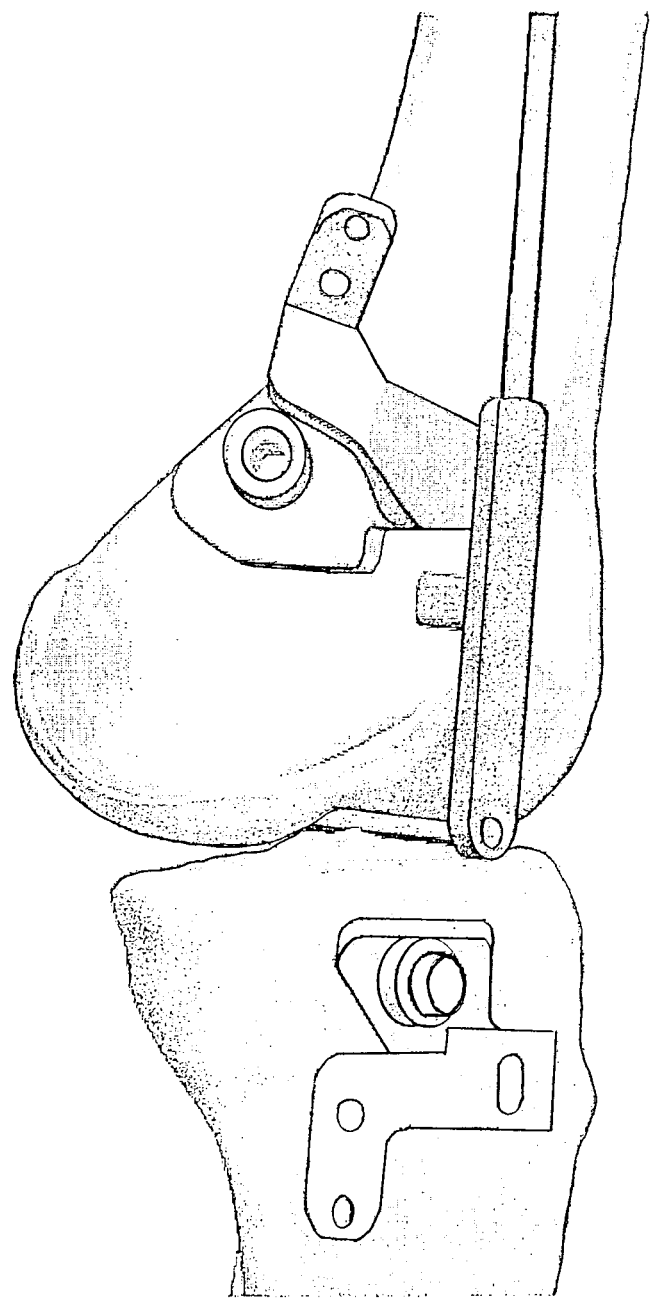
Figure 17:
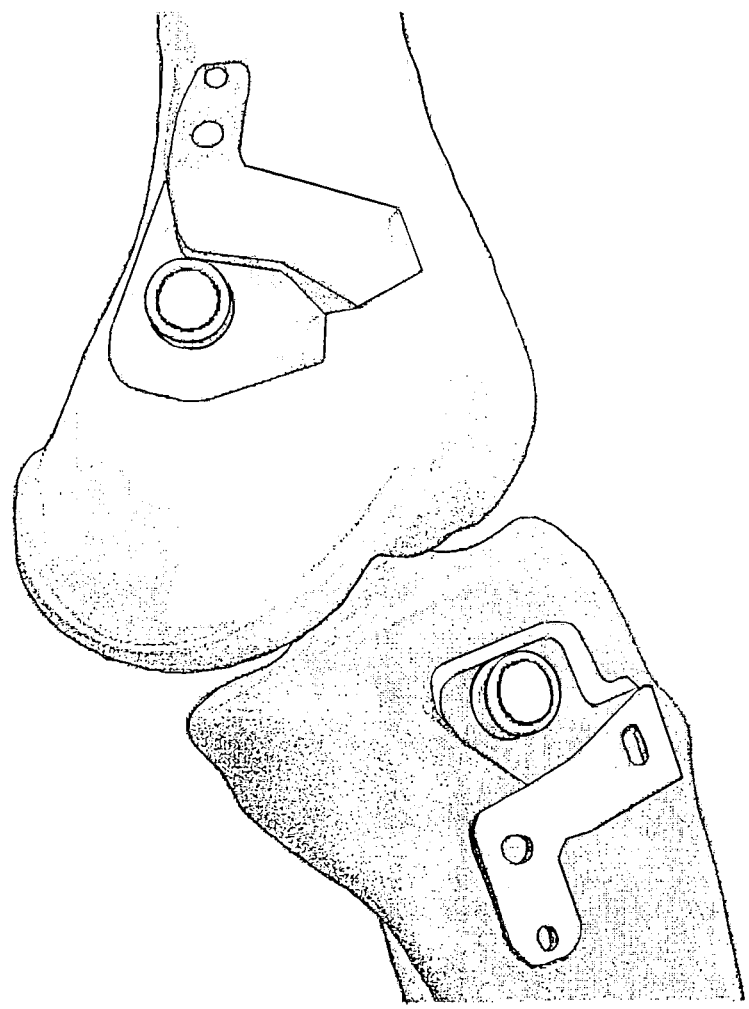

As shown in FIG. 11, the ligament-balancing device 12 or spreader can be provided with or connected to an interface 13 in order to receive or attach a femur cutting block 11, which can be the same cutting block as described above. FIG. 12 shows the ligament balancing device 12 inserted into the joint gap with the attached cutting block 11.

FIGS. 13 to 17 show a modified workflow, wherein the array bases are not inserted or attached simultaneously or almost simultaneously, but instead one after another. The positioning tool is formed like a rod having preferably a circular cross section, so that the tool can be rotated around the axis of this rod after the first base has been attached to align and attach the second base.

To provide an alignment with respect to the anatomical structures, an aiming device in the form of a long rod can be attached. This rod can be pointed to the femur head or the ankle joint depending on which base is attached. This enables a rough alignment of the bases, since the desired cutting plane is measured with respect to the mechanical leg axis, which runs from the femur head to the ankle joints.

Figure 18:
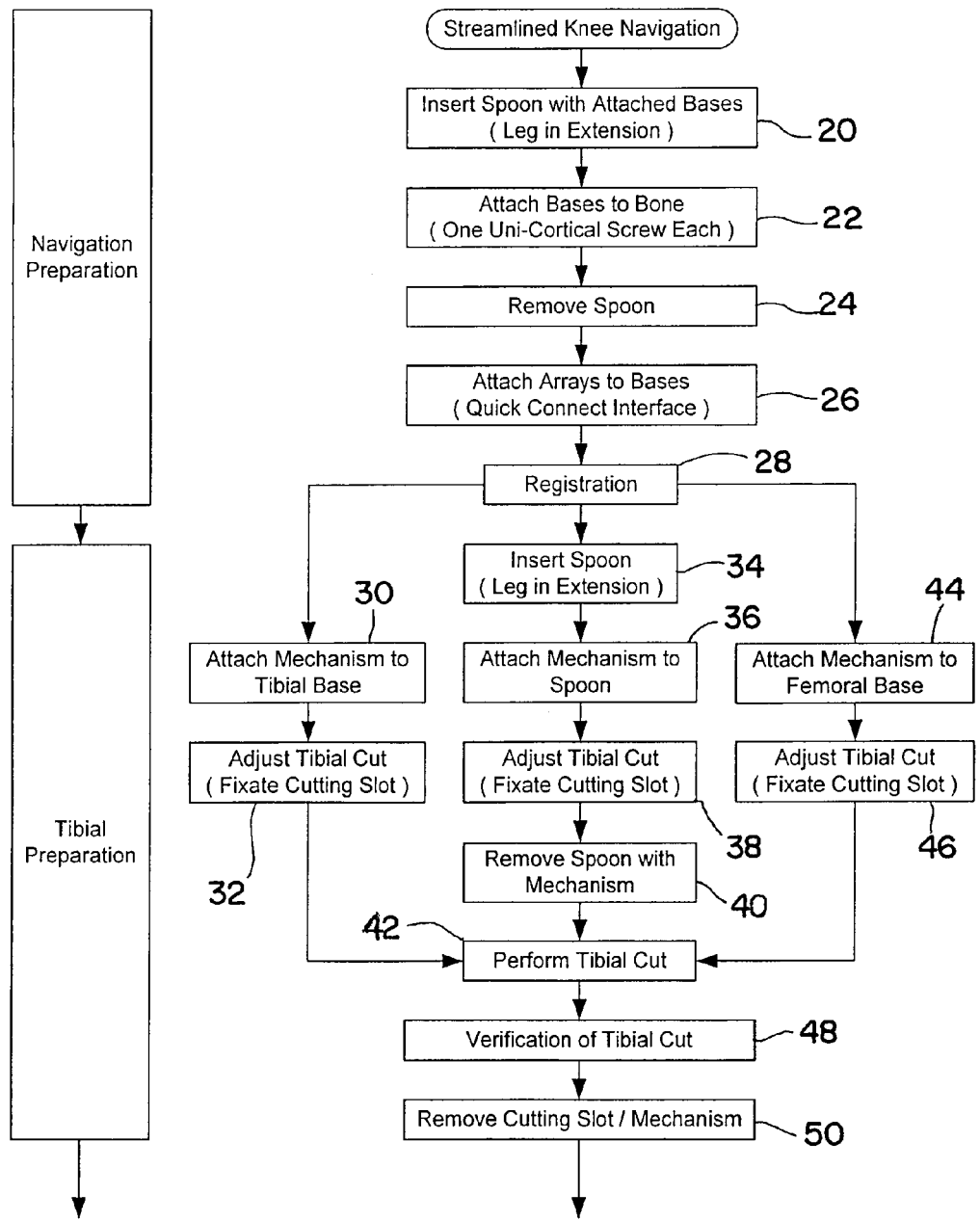
FIG. 18 shows a first part of an exemplary workflow for a streamlined knee navigation in accordance with the invention.
Figure 19:
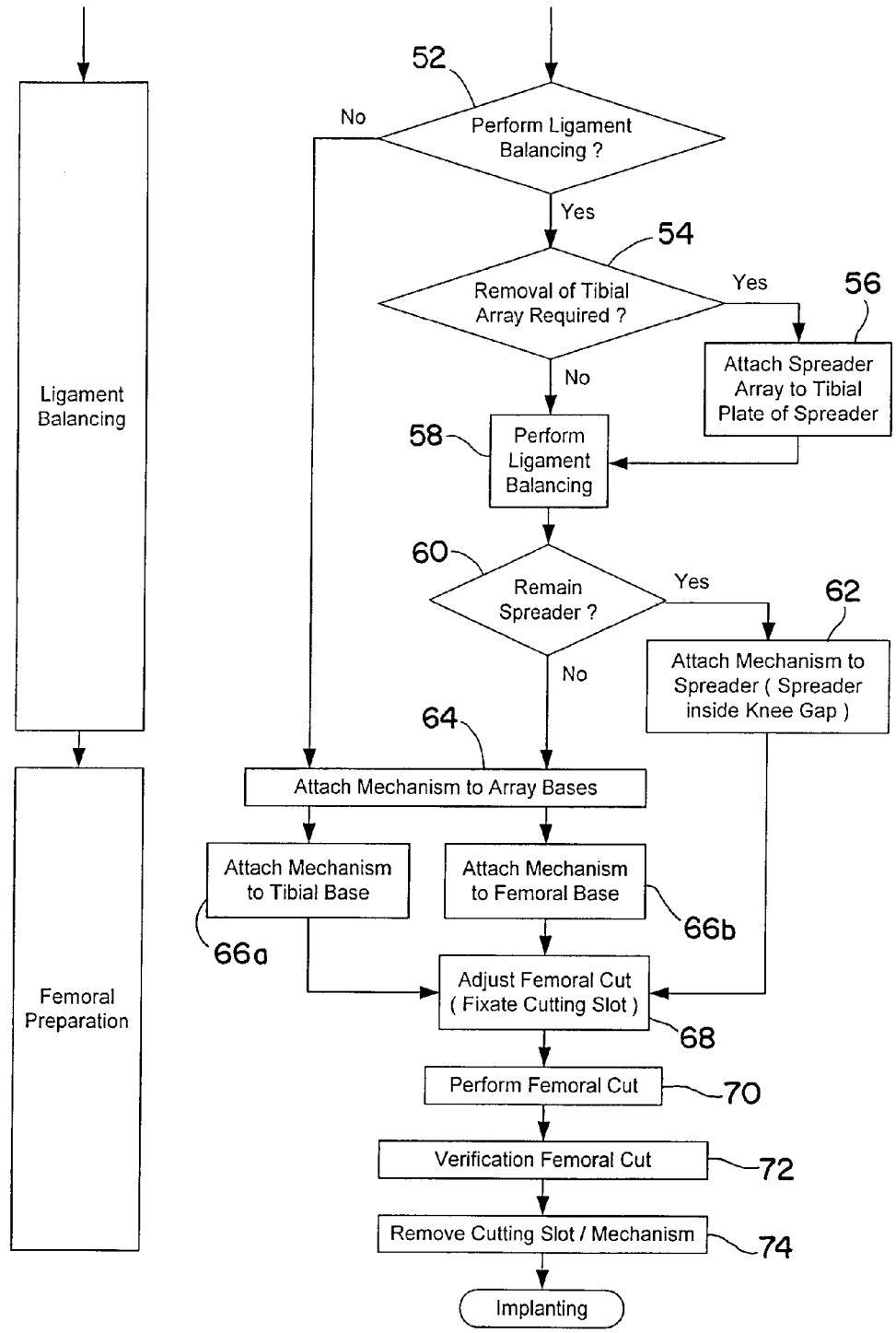
FIG. 19 shows a second part of an exemplary workflow in accordance with the invention.
Figure 20A:
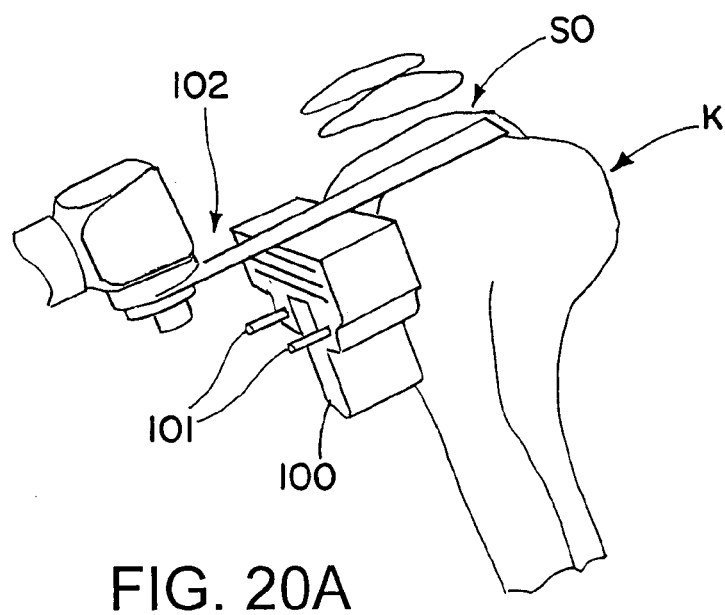
FIGS. 20A and 20B show the incision of a bone using a first cutting block positioned in accordance with the prior art.
Figure 20B:
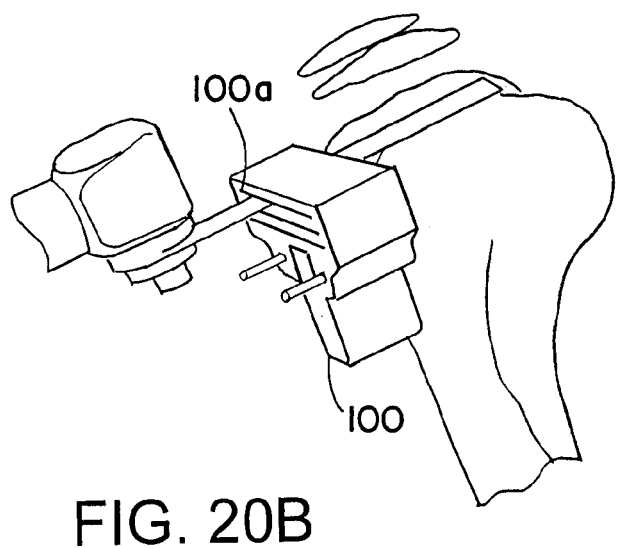
Figure 21:
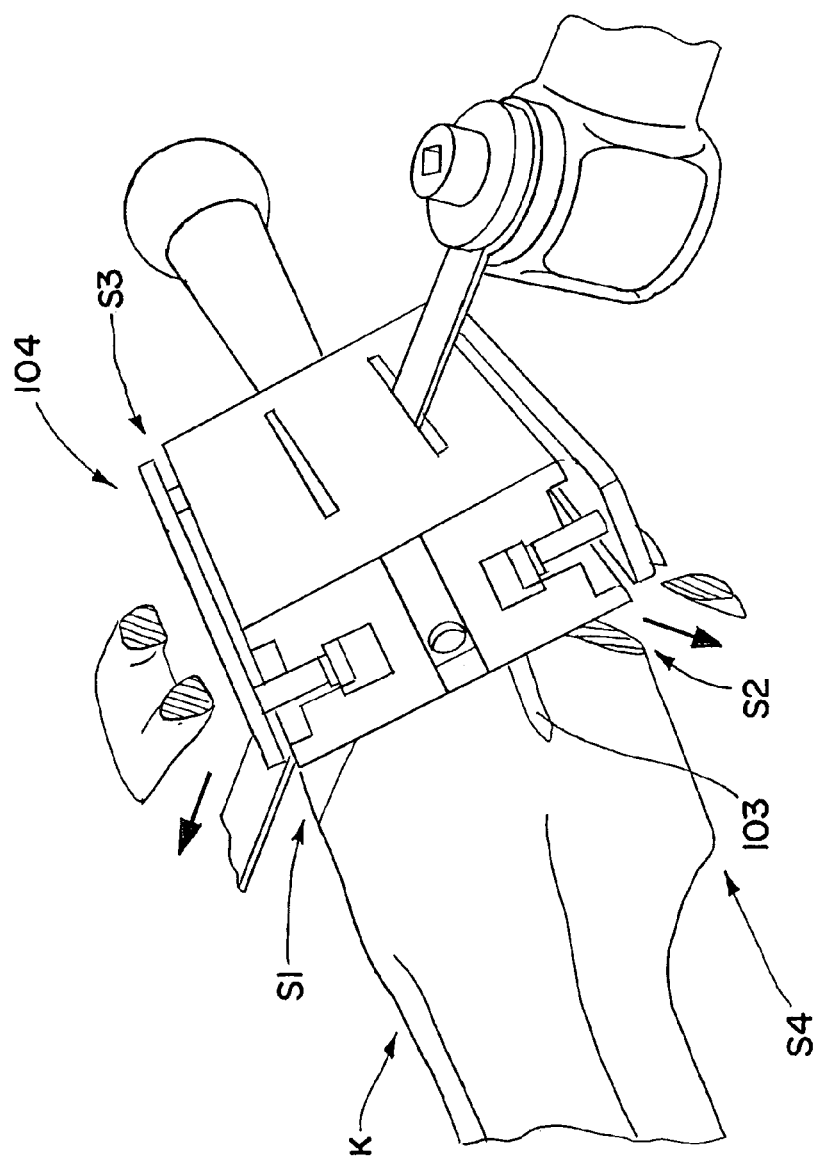
FIG. 21 shows the generation of further incision planes S1 to S4 using a second incision block positioned in accordance with the prior art.

FIGS. 18 and 19 show an exemplary workflow, which can be divided into the four basic steps of: Navigation/Preparation, Tibial Preparation, Ligament Balancing and Femoral Preparation.

Starting with the streamlined knee navigation, the first step of navigation/preparation is inserting the recessed positioning tool 1 with the attached bases 3a and 3b while the leg is in an extended state, as indicated at block 20. Thereafter, at block 22 the bases 3a and 3b are attached to the bone(s) 4 and 5 using a single uni-cortical screw 8 for each bone, as shown in FIG. 4. At block 24, the recessed positioning tool 1 is removed and at block 26 the reference arrays 10a and 10b are attached using a quick connect interface 10c to the bases 3a, 3b, as shown in FIGS. 6 and 7. At block 28 a registration procedure is performed, as is known in the art.

In principal three possibilities exist to prepare the tibial cut 5a shown in FIG. 12. One possibility is to attach a cutting block 11 or cutting mechanism to the tibial base 3b as shown at block 30. Then at block 32 the cutting block 11 is adjusted to thus adjust the tibial cut 5a and to fixate the cutting block 11, e.g., using holes 11d, 11e.

A further possibility is to re-insert the positioning tool 1 with the slidable element 2, or the element 2 being attached or fixed thereto while the leg is still in extension as indicated at block 34. Then at block 36 the cutting mechanism or cutting block 11 is attached to the positioning tool 1 or element 2, and to adjust the cutting block 11 or mechanism at block 38 to thereby adjust the tibial cut 5a. Thereafter, the recessed positioning tool 1 and element 2 is removed at block 40 and the tibial cut 5a is performed at block 42.

A further possibility exists according to which the cutting block 11 or mechanism is attached to the femoral base 3a, as indicated at block 44. Then, the tibial cut 5a is adjusted as indicated at block 46. Thereafter, the tibial cut 5a is performed.

At block 48, the tibial cut 5a can be verified and at block 50 the cutting slots or cutting block 11 or cutting mechanism can be removed. Thereafter at block 52 ligament balancing can optionally be performed, wherein the tibial array 10b may need to be removed (block 54) to attach the spreader array 10c (block 56) to the tibial plate 12a of the spreader 12. Thereafter ligament balancing is performed at block 58 as is known in the art.

In case the spreader 12 remains attached, as indicated at block 60, a mechanism can be attached to the spreader 12 (block 62) and thereafter the femoral cut can be adjusted at block 68. In case the spreader 12 does not remain in the joint, then at block 64 a mechanism or cutting block 11 is attached to one of the array bases before the femoral cut is adjusted. It is also possible that the cutting block 11 or mechanism can be attached to the tibial and the femoral base, before the femoral cut is adjusted, as indicated at blocks 66a and 66b. Thereafter, the femoral cut is performed, verified and the cutting slot or cutting mechanism is removed as indicated at blocks 68, 70, 72 and 74.

Once femoral preparation is complete, the implanting procedure can be begin so as to implant the artificial joint, as known in the art.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A positioning device for aligning at least two supports on at least two bones of a patient, comprising:
    a positioning tool defining a planar extent that defines a plane and has a first planar surface and a second planar surface, the positioning tool configured such that the first and second planar surfaces interface simultaneously with a part of both of the at least two bones so as to establish a reference position relative to the at least two bones; and
    a positioning element having a middle portion including an aperture, the aperture slidably supported on and guided by the first and second planar surfaces of the positioning tool for movement along a length of the positioning tool, a first arm unitary with the middle portion and projecting from a first side of the middle portion in a first direction and a second arm unitary with the middle portion and projecting from a second side of the middle portion in a second direction opposite the first direction, the first and second arms having respective ends, the respective ends being located predetermined distances from said positioning tool when the positioning element is supported on and guided by the positioning tool, the respective ends operative to establish locations on the at least two bones relative to the reference position, wherein the respective ends of the first and second arms are releasably couplable to respective ones of the at least two supports, such that the respective ends of the first arm and the second arm may be removed from the at least two supports while the at least two supports are fixed to the at least two bones.

2. The positioning device according to claim 1, wherein the portion of the positioning tool configured to interface with the part of one of the at least two bones comprises an elongated part having a recessed surface.

3. The positioning device according to claim 2, wherein the recessed surface has a generally concave shape.

4. The positioning device according to claim 1, wherein the positioning element is slidable, movable or relocatable on or with respect to the positioning tool.

5. The positioning device according to claim 1, wherein the first and second arms include at distal ends thereof at least one pin configured to couple to at least one hole on one of the supports or at least one hole configured to couple to at least one pin on the support.

6. The positioning device according to claim 1, wherein the first and second arms are formed to allow connection in only a single predefined orientation of the at least two supports relative to the positioning element.

7. A positioning system for aligning or positioning at least one support at one or more bones, comprising:
    the positioning device according to claim 1; and
    at least one support comprising a coupling element operative to be releasably coupled to one of the first or second arms of the positioning element.

8. The positioning system according to claim 7, wherein the coupling element of the support comprises a hole or a pin.

9. The positioning system according to claim 7, wherein the at least two supports comprise a surface that interfaces with the bone, said surface having projections or serrations that prevent movement of the support relative to the bone.

10. The positioning system according to claim 7, further comprising a drill guide attachable to the at least two supports.

11. The positioning system according to claim 7, further comprising at least one reference array attachable to the at least two supports.

12. The positioning system according to claim 7, further comprising a cutting block attachable to the at least two supports.

13. The positioning system according to claim 1, wherein the middle portion and the first and second arms are a single element.

14. The positioning system according to claim 1, wherein the middle portion is a tubular member defining a through slot that surrounds the positioning tool.

15. The positioning system according to claim 1, wherein the first and second arms are directly releasably couplable to respective ones of the at least two supports.

* * * * *